United States Patent [19]

Weiss

[11] Patent Number: 4,883,351

[45] Date of Patent: Nov. 28, 1989

[54] APPARATUS FOR THE DETECTION OF DIABETES AND OTHER ABNORMALITIES AFFECTING THE LENS OF THE EYE

[76] Inventor: Jeffrey N. Weiss, 77 Pond Ave., Brookline, Mass. 02146

[21] Appl. No.: 671,520

[22] Filed: Nov. 15, 1984

Related U.S. Application Data

[62] Division of Ser. No. 416,654, Sep. 10, 1982, abandoned.

[51] Int. Cl.$^4$ ............................................... A61B 3/10
[52] U.S. Cl. ...................................... 351/221; 351/214
[58] Field of Search ................. 351/210, 211, 214, 221

[56] References Cited

U.S. PATENT DOCUMENTS 4,477,159 10/1984 Mizuno et al. ....................... 351/214

OTHER PUBLICATIONS

Tanaka et al., Investigative Ophtalmology and Visual Science, vol. 16, pp. 135–140, Feb. 19, 1977.

Primary Examiner—Bruce Y. Arnold
Assistant Examiner—P. M. Dzierzynski
Attorney, Agent, or Firm—Wolf, Greenfield & Sacks, P.C.

[57] ABSTRACT

Apparatus for detecting the presence of diabetes mellitus and other abnormalities affecting the lens of the eye and for monitoring eye lens changes resulting from that disease or from other causes is disclosed. The apparatus enables the diffusion coefficient of the lens of a patient's eye to be ascertained by directing a light beam from a low-power laser at the patient's lens and measuring fluctuations in intensity of the back-scattered light caused by the movement of light scatterers in the lens. The apparatus is arranged to give a three dimensional view of the light-scattering site in the lens of the eye from which a measurement is taken and employs a binocular microscope having a fiber optic situated in one eyepiece of the microscope. Back-scattered light is focused by that eyepiece on the fiber optic while enabling the site in the lens to be stereoptically viewed.

3 Claims, 2 Drawing Sheets

APPARATUS FOR THE DETECTION OF DIABETES AND OTHER ABNORMALITIES AFFECTING THE LENS OF THE EYE

CROSS-REFERENCE TO RELATED APPLICATIONS

This application is a division of my parent patent application Ser. No. 416,654, now abandoned filed Sept. 10, 1982. continuation of the parent patent application was filed on Nov. 19, 1984 and has been given Ser. No. 672,717

FIELD OF THE INVENTION

This invention relates to medical diagnostic and monitoring apparatus and, in particular, to apparatus for detecting and monitoring diabetes mellitus and other abnormalities affecting the lens of an eye.

BACKGROUND OF THE INVENTION

Diabetes mellitus is one of the leading causes of morbidity and mortality in the United States. Although the disease, once diagnosed, can be controlled, the diabetic patient faces many complications, some of them life-threatening. For example, the average life expectancy of the diabetic patient is one third less than that of the general population; blindness is twenty five times as common, renal disease is seventeen times more common, gangrene is five times as common and heart disease is twice as common in diabetics as compared to the non diabetic.

In addition, the incidence of this disease appears to be increasing—between 1936 and 1978 there was a six fold increase in the prevalence of the disease.

It is believed by many researchers in the field that many complications suffered by diabetic patients can be minimized or avoided by early detection of the onset of the disease and proper long-term control of the patient's blood glucose.

Unfortunately, prior art detection and monitoring methods and apparatus has been unable to either accurately detect the onset of the disease at an early stage or assess the degree of control on a long-term basis. Such prior art detection methods, other than interpretation of clinical symptoms, rely on blood sugar measurements which reflect the presence of the disease. Prior art monitoring methods involve either spot blood sugar measurements or more complicated blood tests which reflect blood glucose levels that existed in the patient's body at a time three to five weeks prior to the time of measurement. Both prior art measurement methods require bodily invasion and the results are difficult to interpret.

Accordingly, it is an object of this invention to provide apparatus to detect the onset of diabetes mellitus prior to the appearance of clinical symptoms.

It is another object of this invention to provide apparatus for the detection of abnormalities affecting the lens of the eye.

It is still another object of this invention to provide apparatus which facilitates assessment of the effectiveness of various methods of diabetic treatment.

It is yet another object of this invention to provide apparatus which conduces to the ascertainment of the degree of control required to prevent the occurrence of diabetic complications.

It is a further object of this invention to provide an apparatus which enables the effects of systemic disease, trauma, drugs, local inflammatory conditions of the eye, and aging to be quantified by measurements taken from the lens of an in vivo eye.

SUMMARY OF THE INVENTION

The foregoing objects are achieved and the foregoing problems are solved in one illustrative embodiment of the invention in which the diffusion coefficient of the lens of a patient's eye is measured by directing the beam from a low-power laser at the patient's lens and measuring the intensity of the back-scattered light. A number of measurements are taken of the diffusion coefficient for patients known to be normal to establish a diffusion coefficient-age relationship. The lens diffusion coefficient of an unknown patient is compared to the pre-established relationship and a significant decrease of lens diffusion coefficient over the normal diffusion coefficient-age relationship indicates a likelihood of diabetes. The amount of decrease of lens diffusion coefficient over the normal pre-established diffusion coefficient can be used to indicate the severity of the disease or monitor the progress and treatment of the disease.

More particularly, the optical system used in illustrative embodiment consists of a low-power laser and associated optics attached to a slit-lamp biomicroscope equipped with precision mechanical adjustments to focus the light beam on a site in the patient's lens. A photomultiplier is used to detect the intensity of light back-scattered from the site and a correlator is used to process the output of the photomultiplier to provide a set of numbers that can be used to calculate the diffusion coefficient.

DETAILED DESCRIPTION OF THE PREFERRED EMBODIMENT

Figure 1:
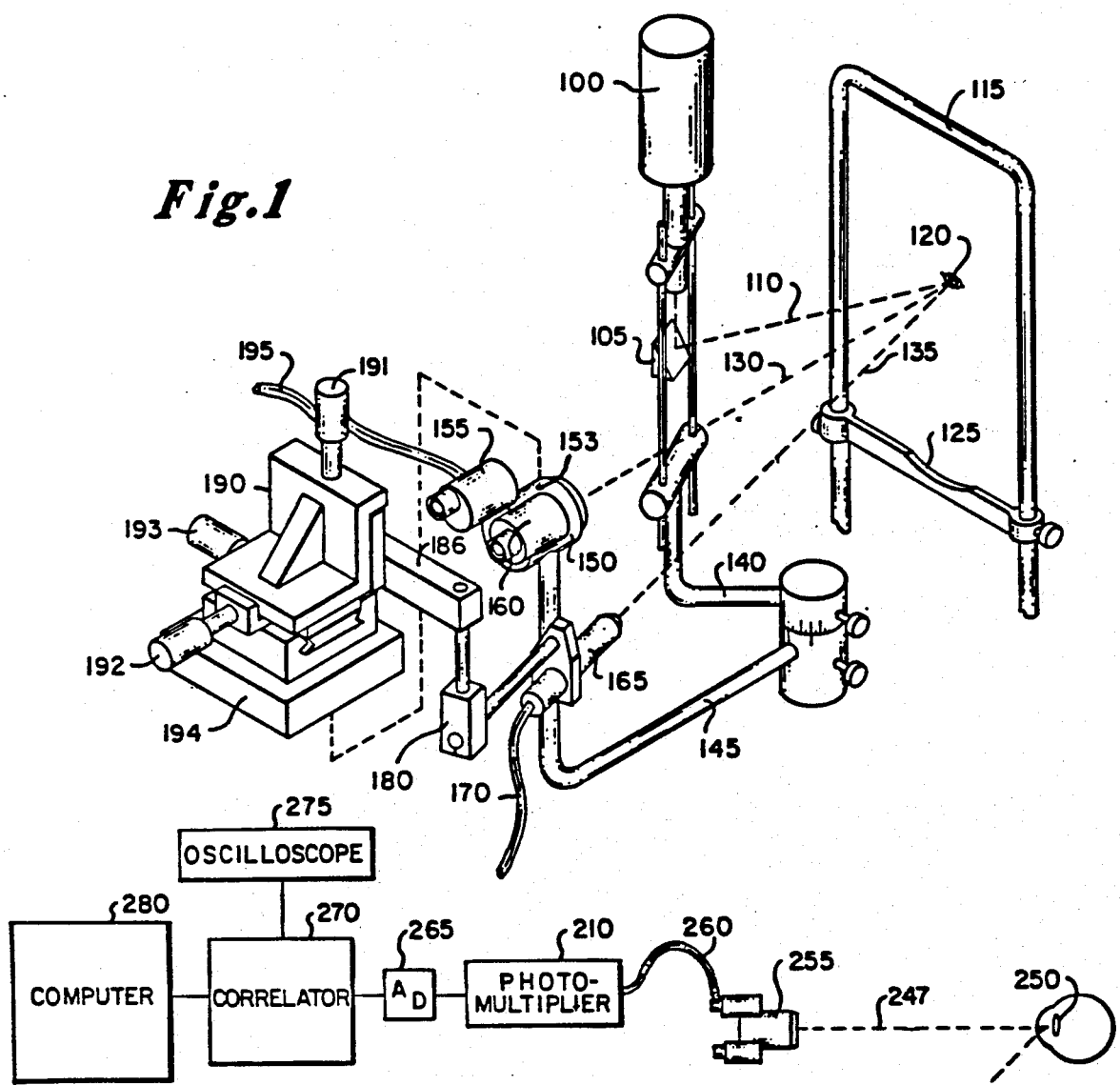
FIG. 1 is a perspective view of the slit-lamp biomicroscope and added equipment used to focus the light beam on a site in the patient's lens.

FIG. 1 shows the mechanical and optical arrangement for an illustrative embodiment of the inventive diabetic detection device. In particular, a suitable arrangement consists of a modification of a commercially-available optical instrument known as a slit-lamp biomicroscope. This device is well-known to those skilled in the art and typically is used in ophthalmological studies of the cornea, lens and retina of the human eye. A device suitable for use with the illustrative embodiment is manufactured by several companies and its operation and use are well known to those skilled in the art.

Basically, a slit-lamp biomicroscope consists of a light source, a microscope and a mechanical supporting arrangement which allows precise positioning of the light source and microscope relative to the patient to allow focusing of the light on selected sites in the patient's eye. Specifically, light produced by source 100 is reflected from mirror 105 and directed as beam 110 to the patient's eye shown schematically as eye 120. The apparatus also includes frame 115 and support 125 which position and hold the patient's head in a fixed position. Light which is reflected or scattered by the patient's cornea, lens or retina, shown schematically as beam 130, is received by a binocular microscope arrangement 150 which has two eyepieces, 155 and 160. The lamp arrangement and microscope are supported by arms 140 and 145 from a common post, all in a well-known manner.

In accordance with the invention, the standard slit-lamp biomicroscope is modified by the addition of an XYZ positioning apparatus to the microscope arrangement 150. In particular, the XYZ position apparatus consists of commercial XYZ positioner 190 which can obtain precise three-dimensional movement which is controlled by three orthogonal micrometers, 191–193. Positioner 190 is mounted on plate 194 which is in turn fastened to microscope arrangement 150 by means of a threaded hole 153 which is normally found on the arrangement and used for other purposes.

Attached to the movable surface of XYZ positioner 190 are arms 180 and 186 which support a lens arrangement 165. As will be hereinafter further explained, lens arrangement 165 is connected via fiber optic cable 170 to a laser and used to illuminate the patient's lens via beam 135. The back-scattered light shown schematically as beam 130 is detected by a sensor located in the focal plane of eyepiece 155 and conveyed via cable 195 to a photomultiplier (not shown).

Figure 2:
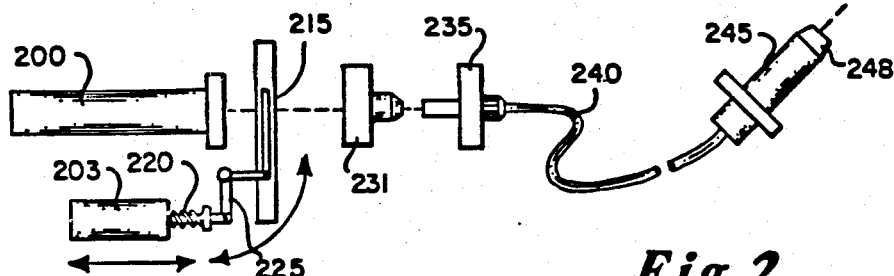
FIG. 2 shows an overall schematic view of the optical arrangement to irradiate a site in the patient's lens and the apparatus used to process the resulting signal.

FIG. 2 of the drawing shows a schematic diagram of the entire optical arrangement of the present invention. The apparatus consists of an irradiating portion or light source for illuminating the patient's lens and a detecting or receiving portion for receiving the back-scattered radiation.

The light source part of the apparatus consists of laser 200, two filters mounted in housing 215, microscope objective lens 231, fiber optic termination 235, fiber optic cable 240 and focusing lens arrangement 245. Laser 200 is a 5 milliwatt helium-neon laser of conventional design which is commercially available from several companies. A laser suitable for use with the illustrative embodiment is a model U-1305P manufactured by the Newport Corporation, 18235 Mount Baldy Circle, Fountain Valley, Calif. The output of laser 200 passes through two neutral density filters, mounted in housing 215. One filter is permanently mounted in the laser beam path and reduced the power output of laser 200 to 1.5 milliwatts. The other filter is solenoid-controlled so that it can automatically be moved out of the laser beam path during the measurement operation. When both filters are in place, they reduce the laser output power to 0.50 milliwatts. The movable filter is used during premeasurement focusing, as will hereinafter be described, in order to reduce the patient's exposure to unnecessary laser irradiation. The movable filter is controlled by solenoid 203 which is under control of a footswitch operated by the person making the measurement. When solenoid 203 is operated, arm 220 retracts, in turn, sliding the movable filter in housing 215 by means of bell-crank 225.

After passing through one or both filters the attenuated laser output light enters lens 231. Lens 231 is a 40× microscope objective lens which is mounted so that it focuses the laser light on he end of the optical fiber which transmits the light to the irradiating apparatus. Light passing through lens 231 falls onto an optical fiber 240 mounted in termination 235. The end of fiber 240 which enters termination 235 is attached to an XYZ positioner. The positioner is used to align the end of the optical fiber with the focusing lens to obtain maximum light transmission.

The other end of optical fiber 240 is attached to focusing lens arrangement 245. Lens arrangement 245 consists of a fiber optic holder which is slidably mounted in a lens holder tube. Lens 248 is a 18 mm focal-length converging lens which is mounted at the other end of the lens holder tube. The movable arrangement between the fiber optic holder and the lens allows small adjustments to be made between the end of the optical fiber and the lens to permit fine focusing of the laser output beam at a given position within the patient's lens.

Lens arrangement 245 is connected to the XYZ positioner attached to the slit-lamp biomicroscope as previously described and is used to focus the laser beam, 246, such that a sharp focus is achieved at the patient's lens 250. After passing through the focal point in the lens the beam becomes sharply defocused in order to maintain a low irradiation level at the retina and prevent any possibility of injury or damage.

The detection optical system uses portions of the optical system of the slit-lamp biomicroscope. In particular, light back-scattered from the patient's lens (represented schematically as beam 247) is focused by one objective of the binocular portion of microscope 255 onto a commercially-available optical fiber light guide, 260, located at the center of the focal point of the eyepiece. In the illustrative embodiment, the end termination of optical fiber light guide 260 replaces the normal left ocular of slit-lamp biomicroscope 255. The arrangement is such that the end of fiber cable 260 can be seen when looking through the left ocular to allow focusing of the back-scattered radiation on the end of the fiber cable. Scattered light received at microscope 255 is fed by fiber optic guide 260 to photomultiplier 210 which is a well-known, commercially-available device. A photomultiplier suitable for use with the illustrative embodiment is a model number 9863B/350 manufactured by EMI Gencom, Inc., 80 Express Street, Plainview, N.Y. The output of photomultiplier 210 is provided to amplifier-discriminator 265 which also is a well-known device that amplifies the output pulse signals produced by the photomultiplier and selectively sends to correlator 270 only those signals which have an amplitude above a preset threshold. A suitable amplifier-discriminator for use with the illustrative embodiment is a model number AD6 manufactured by Pacific Photometric Instruments, Inc., 5675 Landregan Street, Emeryville, Calif.

The output of amplifier-discriminator 265 is, in turn, provided to a commercial photon correlation spectrometer 270 (a suitable spectrometer is a model DC64 manufactured by Langly-Ford Instruments, 85 North Whitney Street, Amherst, Mass.). Correlator 270 counts the number of pulses received from amplifier-discriminator 265 for a predetermined time interval and performs a well-known mathematical operation to obtain the correlation function. In the illustrative embodiment a suitable time interval is ten microseconds. The correlator utilizes these received counts to solve the following equation for the autocorrelation function $C_m(t)$:

$$C_m(t) = \sum_{i=1}^{i=n} p_i p_{i+m}$$

where
- t = the length of the predetermined time interval
- i = an index number whose range is one to the total number of intervals.
- $p_i$ = the number of pulses occurring during the ith time interval.
- n = the total number of intervals.
- m = an integer whose range is one to sixty-four.

In accordance with the above equation, correlator 270 produces solutions or points (one for each value of m) in a time sequence, each measurement separated by the value of t. These measurements may be plotted against time to produce a curve which may then be displayed for examination on oscilloscope 275. The values of the solutions may also be provided to computer 280 for further processing to determine the diffusion coefficient. A computer suitable for use with the illustrative embodiment is a personal computer manufactured by the International Business Machines Corporation, Armonk, New York.

In particular, the diffusion coefficient (D) is also related to the correlation function $C_m(t)$ determined by the correlator by the following equation:

$$C_m(t) = A + Be^{-2DK^2 m(t)}$$

where
- A, B = constants dependent on the physical details of the measurement
- K = the scattering constant for the eye which is $4\pi/\lambda (\sin \theta/2)$ where $\lambda$ is the wavelength and $\theta$ is the scattering angle
- t = the length of the predetermined time interval
- m = an integer whose range is one to sixty-four.

Therefore, the values of the diffusion coefficient D and the constants A and B in the above equation can be determined, with the aid of computer 280, from the autocorrelation curve produced by the correlator 270 by using standard curve fitting and analysis techniques. The calculated diffusion coefficient can be stored in the computer along with other patient data including, in accordance with the invention, the patient's age.

The apparatus shown in FIGS. 1 and 2 is used to perform a measurement of the lens diffusion coefficient as follows: with a patient sitting at the slit-lamp biomicroscope, the operator sets up the device in the same way that the device would be set up during a normal ophthalmic evaluation. In order to take measurements from various sites within the patient's lens, it is necessary that the pupil be dilated using routinely-available dilating drops as normally used during the course of a complete ophthalmic evaluation. Both the light produced by lamp 100 and the laser light with both filters in place are used to align the laser output as seen through the ocular 155 and 160 with the end of optical fiber light guide 195 in left ocular 155. Due to the standard adjustments on the biomicroscope and XYZ positioner 190, this alignment may be achieved at any desired site within the patient's lens.

Lamp 100 is then turned off and the operator depresses a foot switch which operates solenoid 203, sliding the movable filter in housing 215 out of the way to allow the actual measurement to be made using 1.5 milliwatts laser light power. A second foot switch adjacent to the first can be used to turn laser 200 off should any emergency arise.

The back-scattered light output is measured by the photomultiplier through the optical system previously described and the photomultiplier output is processed as previously described by the photon correlation spectrometer. While measurements are in progress, the output of the spectrometer may be monitored by the oscilloscope connected to it. A measurement is made, for example, for 5 seconds at which point the first foot switch is released, reinserting the movable filter into the optical path, and concluding the measurement.

No contact lens, nor anesthetic drops are necessary to make a measurement. Although commonly used in eye examinations, anesthetic drops have various deleterious side effects. Such side effects include stinging, burning and conjunctival redness as well as severe allergic reactions with resulting central nervous system stimulation or corneal damage. In addition, application of a contact lens following the use of a topical anesthetic requires much patient cooperation as well as experience on the part of the examiner. Further complications arising from the use of a contact lens include corneal abrasions and infection as well as recurrent and chronic corneal erosions. In contrast, the use of the apparatus disclosed herein is truly "non-invasive".

Figure 3:
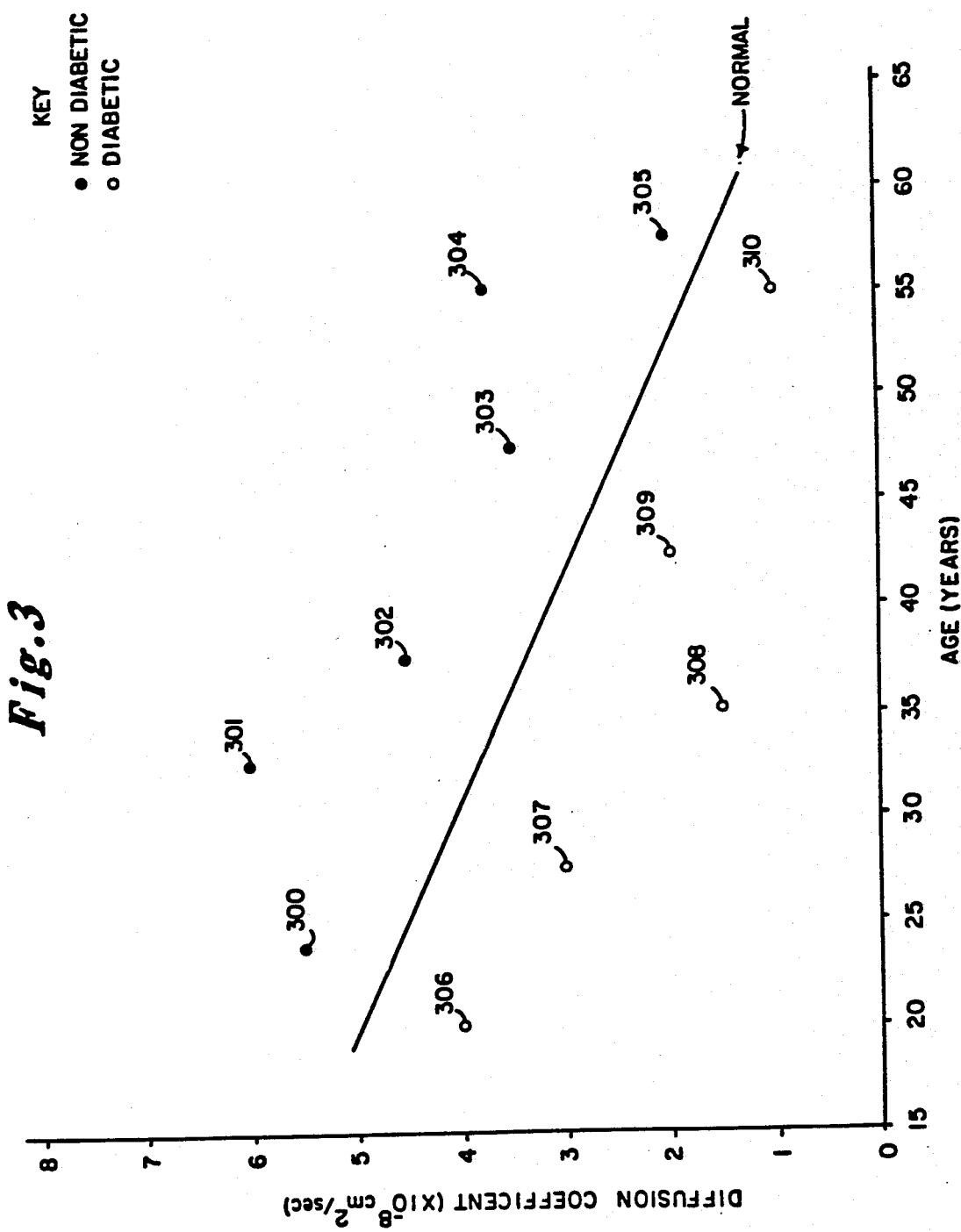
FIG. 3 shows a graph of lens diffusion coefficient versus patient age developed using the apparatus of the present invention which graph is useful in detecting and monitoring diabetes.

When employing the foregoing measurement technique to detect or monitor diabetes, a calculation of the diffusion coefficient s made on a series of patients whose health is known and are believed to be nondiabetic. The resulting measurements are compared to the patient's age resulting in a curve or graph similar to that shown in FIG. 3 (hypothetical measurements are shown for illustrative purposes). FIG. 3 shows the value of the diffusion coefficient increasing in an upwards direction along the vertical axis and patient age increasing rightward in the horizontal direction.

It has been discovered that patients who do not have diabetes (represented for example by points 300–305) all lie above a line (marked "normal" on the graph) while those patients suffering from diabetes lie below the line (represented by points 306–310). In addition, the severity of the disease is directly related to the distance below the line at which the measurement lies which increasing distance indicating increasing severity. For example, the patient represented by point 308 usually exhibits more severe symptoms than the patient represented by point 310.

After a curve such as that shown in FIG. 3 is obtained, patients can be screened for diabetes by making a measurement using the apparatus and method described above. The result of the measurement is then compared to FIG. 3. If the measurement is significantly below the "normal" line as shown in FIG. 3 the patient is likely to have diabetes or a disease which affects the lens similarly. Known diabetic patients can be monitored by making repeated measurements over a fixed period of time. The series of measurements are compared to the graph. An increasing distance from the "normal" line indicates an acceleration in the disease. A fixed distance indicates the disease appears to be under reasonable control.

Although only one illustrative embodiment is shown of the invention, other changes and modifications within the spirit and scope of the invention will be apparent to those skilled in the art. Such modifications and changes are intended to be covered by the claims herein.

I claim:

1. In apparatus for measuring the movement of light scattering elements in the lens of an in vivo eye where the apparatus is of the type having (a) means for providing a beam of light,
(b) means for focusing the light beam on a site in the lens of the eye,
(c) a photomultiplier,
(d) optical means for transmitting light back-scattered from the eye's lens to the photomultiplier, and
(e) correlator means for providing an output that is an autocorrelation function of light intensity variations affecting the photomultiplier's output, the improvement wherein
  the optical means for transmitting light back-scattered from the eye's lens to the photomultiplier is an optical fiber having a light receiving input end, and the improvement further comprises
  (i) a binocular microscope for providing a stereoscopic view of the site at which the light beam is focused in the lens, the optical axis of the binocular microscope being directed at an angle to the light beam sufficient to provide depth perception, and
  (ii) the optical fiber having its input end disposed to enable the binocular microscope to focus light back-scattered from the eye's lens upon the input end of the optical fiber without impairing the stereoscopic view of the site.

2. The improvement according to claim 1, wherein the input end of the optical fiber is disposed in an eyepiece of the binocular microscope.

3. The apparatus according to claim 2, wherein the means for providing a beam light is a laser,
and wherein the improvement further comprises
  (iii) a slit lamp for providing a beam of light in addition to the laser's beam, the slit lamp being parfocal with the laser.

* * * * *